(12) United States Patent
Shuai et al.

(10) Patent No.: US 9,339,053 B2
(45) Date of Patent: May 17, 2016

(54) PREPARATION PROCESS OF A SELF-REINFORCED STARCH COMPOSITE USED TO PRODUCE CAPSULES

(71) Applicant: Zhongshan Capsule Starch Material Technology Co., Ltd., Zhongshan (CN)

(72) Inventors: Fangwen Shuai, Changsha (CN); Nuozi Zhang, Changsha (CN); Xiangfeng Wang, Changsha (CN); Jiawei Zhang, Changsha (CN)

(73) Assignee: Zhongshan Capsule Starch Material Technology Co., Ltd. (CN)

( * ) Notice: Subject to any disclaimer, the term of this patent is extended or adjusted under 35 U.S.C. 154(b) by 36 days.

(21) Appl. No.: 14/519,656

(22) Filed: Oct. 21, 2014

(65) Prior Publication Data

US 2015/0119471 A1   Apr. 30, 2015

(30) Foreign Application Priority Data

Oct. 26, 2013   (CN) .......................... 2013 1 0510581

(51) Int. Cl.
| | |
|---|---|
| *A23L 1/29* | (2006.01) |
| *A23L 1/00* | (2006.01) |
| *B29C 47/92* | (2006.01) |
| *B29C 47/82* | (2006.01) |
| *A61K 9/48* | (2006.01) |

(52) U.S. Cl.
CPC ............. *A23L 1/0029* (2013.01); *A61K 9/4816* (2013.01); *B29C 47/827* (2013.01); *B29C 47/92* (2013.01); *A23V 2002/00* (2013.01); *B29C 2947/92704* (2013.01); *B29C 2947/92895* (2013.01)

(58) Field of Classification Search
CPC ...................................................... A23L 1/0029
See application file for complete search history.

(56) References Cited

U.S. PATENT DOCUMENTS

| | | | |
|---|---|---|---|
| 6,375,981 | B1 | 4/2002 | Gilleland et al. |
| 6,749,880 | B1 | 6/2004 | Woltjes et al. |

FOREIGN PATENT DOCUMENTS

| | | |
|---|---|---|
| CN | 101245157 A | 8/2008 |
| CN | 101906220 B | 1/2012 |

OTHER PUBLICATIONS

Extended European Search Report for Application No. 14190245.2 dated Apr. 30, 2015.

*Primary Examiner* — Paul Zarek
(74) *Attorney, Agent, or Firm* — Lerner, David, Littenberg, Krumholz & Mentlik, LLP

(57) ABSTRACT

The invention discloses a technical process to prepare a self-reinforced starch composite used to produce capsules. This composite is made by uniformly mixing the matrix phase and the particulate reinforced phase at a proper proportion, the former being one or a combination of the starches selected from the group consisting of oxidized starch, cationic starch and esterified starch; and the latter, cross-linked starch or starch nanocrystals. This composite is processed into the forms of granules, films, or sheets by extrusion method and these different forms of the composite can be used to replace the gelatin as the raw material of capsules because its barrier property, processability, and mechanical properties are significantly improved.

8 Claims, 1 Drawing Sheet

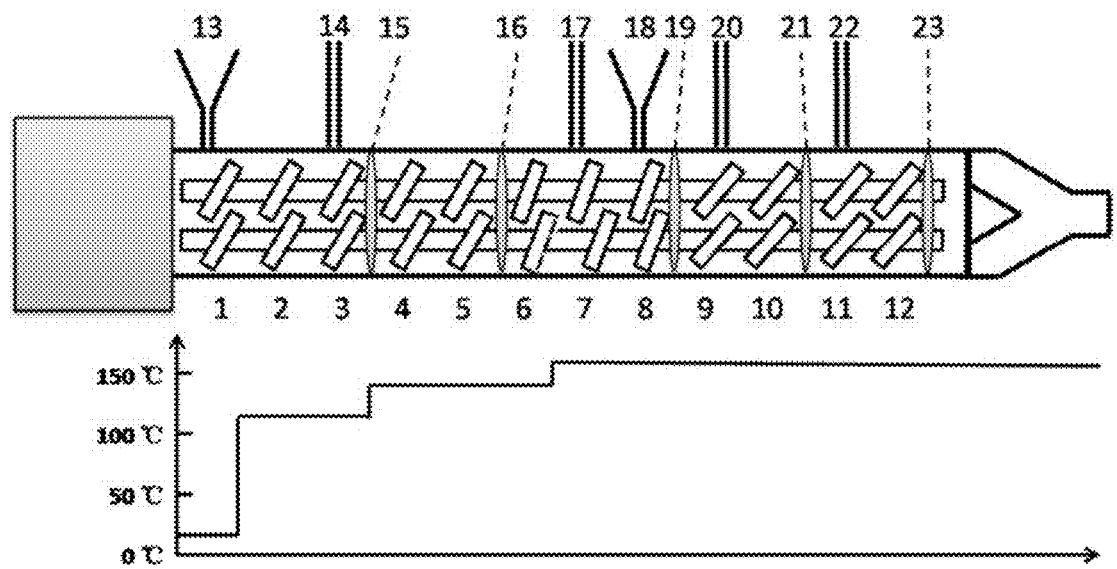

PREPARATION PROCESS OF A SELF-REINFORCED STARCH COMPOSITE USED TO PRODUCE CAPSULES

CROSS REFERENCE TO RELATED APPLICATION

This application claims priority from Chinese Patent Application No. 201310510581.9 filed Oct. 26, 2013, the disclosure of which is hereby incorporated herein by reference.

FIELD OF INVENTION

This invention relates to a preparation process of a self-reinforced starch composite used to prepare capsule products.

BACKGROUND OF THE INVENTION

Capsules are widely used for the products of medicines, dietary supplements and functional foods. Currently in the market, the main material used to manufacture capsule products is gelatin—a product made from animal bones and the skins through hydrolyzation process. Gelatin is a biological triplex structure macromolecule with good biological compatibility and physicochemical properties. The unique molecular structure of the gelatin, however, leads to some disadvantages in its application, one of which is that the gelatin capsule may become less soluble in water as gelatin is easy to crosslink with aldehyde compound, reducing sugar compound, and Vitamin C, resulting in capsule shell disintegration and delay in the dissolving-out of capsule content; another disadvantage is that it produces electrostatic charge accumulation in dry condition, which has negative influences on subsequent processing; finally, if the gelatin capsule is stored in low humidity environment for long time, it may become fragile and easily broken. In addition, because of the animal source component present in gelatin, it is not welcomed by certain groups of people with various faith and religious beliefs. Therefore, it is necessary to research and develop new materials to replace gelatin—the traditional raw material of capsules.

As plant capsule is becoming one of the fastest growing products in pharmaceutical market, the plant materials like gellan gum, carrageenan, and xanthan gum have been used as to study the preparation of the substitute products of gelatin capsules. The starch, with good film-forming properties, is one of the most important food raw materials and has been widely used in the field of food and medicine. With the advantages of rich sources and low price, starch is regarded as a most promising substitute of the raw material of capsules.

Most of the technologies applied in the preparation of starch capsules reported nowadays are similar to the traditional dip forming process to manufacture gelatin capsules. As the gel properties of starch itself can hardly meet the requirements of manufacturing process of capsules, it is, in existing preparation technology, necessary to add certain gel to improve the processing performance in the preparation of starch-based capsules It has been a major research area to improve the mechanical properties and stability of starch-based material. In addition to starch modification, other processing technologies of polymer materials like blending and compounding are also widely used to manufacture starch-based material. In recent years, self-reinforced composites, with perfect material interface, simple chemical structure, and high value-added recycled waste, has attracted wide attention. For Medical biodegradable materials, it is extremely important to use the composite developed by single raw material, because any enhancing or modifying additive is likely to affect the biocompatibility or biodegradability of the main raw material; as a medicinal capsule, the less the amount of additive used, the better. This invention relates to a process for preparing self-reinforced starch composite that can be used to replace the gelatin as the raw material of capsules.

OBJECT OF THE INVENTION

It is therefore an object of the present invention to provide a method for manufacturing self-reinforced starch composite to overcome the existing performance deficiency of starch-based capsule materials.

Another object of the invention is to provide one type of self-reinforced starch composite, and use it to manufacture non-gelatin capsules, in an attempt to overcome the potential risk resulted from the use of gelatin-made capsules and make the capsule products suitable for vegetarians and people of different religious beliefs.

This invention applies a technology for preparing a self-reinforced starch composite that can be used to manufacture capsules. The invention includes the following technical approaches:

Detailed Description of Each Step

Step (a) Matrix phase: One or a combination of the substances selected from the group consisting of oxidized starch, cationic starch, and esterified starch; reinforced phase: cross-linked starch or starch nanocrystals. Uniformly mix the matrix phase and the reinforced phase at the mass ratio of 4:0.01-1.

Step (b) Add the uniform mixture from Step (a) into a double screw-type extruder, heat and knead it, and then add pure water at the amount of 10%-20% of the mixture (by weight) to make the mixture into processable thermoplastic material, which is then extruded into granules or sheets of self-reinforced material or further processed to films.

The matrix phase Step (a) is one or a combination of the substances selected from the group consisting of cationic starch, esterified starch, and oxidized starch from corn, potato, tapioca, wheat, mung bean, and rice, of which, esterified cassava starch is the priority choice. The esterification degree can be 0.001-0.05.

In addition, one type of reinforced matrix according to Step (a) is cross-linked starch, which is one or a combination of the crosslinked starches selected from the group consisting of crosslinked starches extracted from corn, potato, cassava, wheat, mung bean, and rice, of which, cross-linked cassava starch is the priority choice. The cross-linking degree could be 5-45%.

Another type of reinforced matrix according to Step (a) is the starch nanocrystal, which is one or a combination of nanocrystals selected from the group consisting of nanocrystals from corn starch, potato starch, cassava starch, wheat starch, mung bean starch, and rice starch. Starch nanocrystals are prepared by acidolysis of starch using sulfuric acid, and the starch nanocrystals used in this invention are commercially available cassava starch nanocrystals at the particle size of 10-200 nm.

The mass ratio of matrix phase (modified starch) and reinforced phase (cross-linked starch or starch nanocrystals) is as follows:

Modified starch, 98.0%-99.5%; Cross-linked starch or starch nanocrystals, 0.5%-2%.

The pure water described in Step (b) is deionized or purified water.

The said self-reinforced starch composite contains neither gel nor plasticizers, such as polyhydric alcohol or polyhydric sugar alcohol.

The above mentioned composite material is composed of matrix phase, particle reinforced phase, and water. The priority choice for the said matrix phase is esterified cassava starch with esterification degree of 0.001-0.05, and for the particle reinforced phase, the starch nanocrystals at the particle diameter of 10-200 nm.

According to the schematic diagram (FIG. 1), the double-screw extruder is composed of a number of individual cylinder blocks. In the Examples of this invention, there is a selection of 12 independent digit position of each cylinder block, numbered 1 to 12 from the left to the right. Each scrolling block can be electrically heated through a single control circuit or cooled by cooling water. The extruder is a tightly meshed double-screw type with equivalent rotation, and the screw diameter is 50-70 mm, the length to diameter ratio, 36-46, and the compression ratio, 1:2-3. The self-reinforced composite product is fed at the end of the extruder through the nozzle, and a shaping die or casting device is connected to the rear end of the nozzle, Granules or sheets are directly prepared through extrusion at the pressure of 50-2000 N/m2, and the thin film is prepared by tape casting at the casting roller's rotation speed of 1-20 rpm. The prepared self-reinforced composite granules, sheet or film can be directly taken out.

Install kneading discs of different structure at appropriate location on the screw, so to make the raw material mixture kneaded as evenly as possible. As shown in FIGURE, location 1, 13, and 18 are the powdering inlets; location 20 and 14, the injection nozzles, which are used to send fluid to the kneading space; location 15, 16, 19, 21, 23, are the kneading discs; location 17, and 22 are discharge pipes connected to a vacuum source.

FIG. 1 is the temperature curve against each different sliding block in the screw conveyor indicated in the FIGURE. The adjustable accuracy is +/−1° C. One thing needs to be addressed here is that the sliding block and the molten material are not necessarily at the same temperature, and the latter is influenced by the factors like screw speed.

In the Examples of the invention, the model# of the double-screw extruder is TEC52 with screw diameter 51 mm, length to diameter ratio, 40, and compression ratio, 1:2. One thing that needs to be addressed here is that, by properly adjusting the parameters of the extruders, the combination of the matrix phase and the reinforced matrix according to this invention can be used in any single-screw or double screw extruder to make starch self-reinforced composite extrusion granules, films, or sheets.

In the examples of this invention, the screw rotation speed of TEC52 double-screw extruder is set to 300-550 rpm; material feeding speed, 80-250 kg/hour; temperature of block 1, room temperature. The composite material is added in along the moving edge and then introduced into sliding block 2 and 3 which are heated to 60-120° C. In the block 3, the pure water is input at the speed of 20-50 kg/hour, the temperature is raised to 120-140° C. in the closed block 4-6; and in block 7, 5% moisture is taken out by vacuum pump and the temperature is adjusted to 140-160° C.; Connect vacuum to the block 11 to pump out 4% water.

The soft capsule shell manufactured by the self-reinforced starch composite described in this invention can be used for preparing medicines, dietary supplements and functional foods.

FIG. 1: The schematic drawing of the extruder used in the invention

EXAMPLES

The Examples set forth below is illustrative and aims to further explain the invention. It cannot be viewed as limiting the scope of the present invention.

Example 1

Continuously put the following materials into the hopper:
Cassava starch (esterification degree, 0.04): 200 kg/hours
Cross-linking cassava starch (cross-linking degree, about 40%): 50 kg/hour
Add pure water into the sliding block 3 at the speed of 50 kg/hours. Extrude out at the screw rotation speed of 350 RPM and the temperature of the sliding blocks is set as follows:
Sliding Block 1: 25° C.
Sliding Block 2-3: 100° C.
Sliding Block 4-6: 140° C.
Sliding Block 7-9: 160° C.
Sliding Block 10-12: 160° C.
Nozzle: 160° C.

Example 2

Continuously put the following metered materials into the hopper:
Cassava starch (esterification degree, 0.04): 200 kg/hours
Cassava starch nanocrystals (particle diameter, about 180 nm): 50 kg/h
Add pure water into the sliding block 3 at the speed of 50 kg/hours. Extrude out at the screw rotation speed of 350 RPM and the temperature of the sliding blocks is set as follows:
Sliding Block 1: 25° C.
Sliding Block 2-3: 100° C.
Sliding Block 4-6: 140° C.
Sliding Block 7-9: 160° C.
Sliding Block 10-12: 160° C.
Nozzle: 160° C.

Example 3

Continuously put the following metered materials into the hopper:
Cassava starch (esterification degree, 0.04): 200 kg/hours
Cross-linking cassava starch (cross-linking degree of about 40%): 10 kg/h
Cassava starch nanocrystals (particle size about 180 nm): 40 kg/h
Add pure water into the sliding block 3 at the speed of 50 kg/hours. Extrude out at the screw rotation speed of 350 RPM and the temperature of the sliding blocks is set as follows:
Sliding Block 1: 25° C.
Sliding Block 2-3: 100° C.
Sliding Block 4-6: 140° C.
Sliding Block 7-9: 160° C.
Sliding Block 10-12: 160° C.
Nozzle: 160° C.

Example 4

Continuously put the following metered materials into the hopper:
Cassava starch (esterification degree, 0.04): 200 kg/hours Cross-linking cassava starch (cross-linking degree of about 40%): 40 kg/h
Cassava starch nanocrystals (particle size about 180 nm): 10 kg/h
Add pure water into the sliding block 3 at the speed of 50 kg/hours. Extrude out at the screw rotation speed of 350 RPM and the temperature of the sliding blocks is set as follows:
Sliding Block 1: 25° C.
Sliding Block 2-3: 100° C.
Sliding Block 4-6: 140° C.
Sliding Block 7-9: 160° C.
Sliding Block 10-12: 160° C.
Nozzle: 160° C.

Example 5

Continuously put the following metered materials into the hopper:
Cassava starch (esterification degree, 0.04): 200 kg/hours
Cross-linking cassava starch (cross-linking degree, about 40%): 31.25 kg/h
Cassava starch nanocrystals (particle size about 180 nm): 31.25 kg/h
Add pure water into the sliding block 3 at the speed of 50 kg/hours. Extrude out at the screw rotation speed of 350 RPM and the temperature of the sliding blocks is set as follows:
Sliding Block 1: 25° C.
Sliding Block 2-3: 100° C.
Sliding Block 4-6: 140° C.
Sliding Block 7-9: 160° C.
Sliding Block 10-12: 160° C.
Nozzle: 160° C.

Example 6

Continuously add the following materials into the hopper:
Esterified cassava (esterification degree: 0.04): 200 kg/h
Cassava starch nanocrystals (particle size: 80 nm): 50 kg/h
Extrudes out at the screw rotation speed of 350 RPM and the temperature of the sliding blocks is set as follows:
Sliding Block 1: 25° C.
Sliding Block 2-3: 100° C.
Sliding Block 4-6: 140° C.
Sliding Block 7-9: 160° C.
Sliding Block 10-12: 160° C.
Nozzle: 160° C.

Example 7

Continuously add the following metered materials into the hopper:
Cassava starch (esterification degree, 0.04): 200 kg/hours
Cassava starch nanocrystals (particle size about 180 nm): 50 kg/h
Add pure water into the sliding block 3 at the speed of 50 kg/hours. Extrude out at the screw rotation speed of 350 RPM and the temperature of the sliding blocks is set as follows:
Sliding Block 1: 25° C.
Sliding Block 2-3: 120° C.
Sliding Block 4-6: 120° C.
Sliding Block 7-9: 120° C.
Sliding Block 10-12: 120° C.
Nozzle: 120° C.

Example 8

Continuously adds the following metered materials into the hopper:
Cassava starch (esterification degree, 0.04): 250 kg/hours
Add pure water into the sliding block 3 at the speed of 50 kg/hours. Extrude out at the screw rotation speed of 350 RPM and the temperature of the sliding blocks is set as follows:
Sliding Block 1: 25° C.
Sliding Block 2-3: 120° C.
Sliding Block 4-6: 140° C.
Sliding Block 7-9: 160° C.
Sliding Block 10-12: 160° C.
Nozzle: 160° C.

Example 9

Continuously add the following metered materials into the hopper:
Cross-linking cassava starch (degree of cross-linking of about 40%): 250 kg/h
Add pure water into the sliding block 3 at the speed of 50 kg/hours. Extrude out at the screw rotation speed of 350 RPM and the temperature of the sliding blocks is set as follows:
Sliding Block 1: 25° C.
Sliding Block 2-3: 120° C.
Sliding Block 4-6: 140° C.
Sliding Block 7-9: 160° C.
Sliding Block 10-12: 160° C.
Nozzle: 160° C.

Example 10

Continuously adds the following metered materials into the hopper:
Cassava starch nanocrystals (Particle size about 180 nm): 250 kg/h
Add pure water into the sliding block 3 at the speed of 50 kg/hours. Extrude out at the screw rotation speed of 350 RPM and the temperature of the sliding blocks is set as follows:
Sliding Block 1: 25° C.
Sliding Block 2-3: 120° C.
Sliding Block 4-6: 140° C.
Sliding Block 7-9: 160° C.
Sliding Block 10-12: 160° C.
Nozzle: 160° C.

Example 11

Continuously adds the following metered materials into the hopper:
Cassava starch nanocrystals 95%, gel (GUM) 3.45%, plasticizer (glycerol) 1.25%, anti caking agent
(Stearic acid) 0.25%, emulsifier (sodium dodecyl sulfate) 0.05% uniform mixture. Feeding speed, 250 kg/h
Add pure water into the sliding block 3 at the speed of 50 kg/hours. Extrude out at the screw rotation speed of 350 RPM and the temperature of the sliding blocks is set as follows:
Sliding Block 1: 25° C.
Sliding Block 2-3: 120° C.
Sliding Block 4-6: 140° C.
Sliding Block 7-9: 160° C.
Sliding Block 10-12: 160° C.
Nozzle: 160° C.

Table 1: The performance parameter of the self-reinforced starch composite sheets manufactured according to Example 1-11.

The experimental results show that, each performance parameter of the sheet material made from independent esterified starch, cross-linked starch or starch nanocrystals cannot satisfy the requirements of capsule production process, and when the right amount of gel and plasticizer is added, the performance of the sheet material will be improved significantly to meet the requirements. The self-reinforced starch composite processed by this invention is made by appropriate proportion of different materials with no gel agent and plasticizer added at all, and the final products of self-reinforced starch composite films or sheets therefrom can satisfy the requirements of capsule production process.

TABLE 1

Performance index of the sheet material manufactured using different methods

| Example # | Young's modulus MPa | Tension intensity MPa | Percentage of breaking - elongation % | Moisture % | Co-efficient of viscosity MFI | Thickness mm |
|---|---|---|---|---|---|---|
| 1 | 4.0 | 70.2 | 80.4 | 20.2 | 0.61 | 0.54 |
| 2 | 3.9 | 69.4 | 76.8 | 19.5 | 0.57 | 0.55 |
| 3 | 4.1 | 70.4 | 83.1 | 20.6 | 0.59 | 0.55 |
| 4 | 4.3 | 73.4 | 82.1 | 22.5 | 0.57 | 0.54 |
| 5 | 4.6 | 78.9 | 86.5 | 21.6 | 0.58 | 0.55 |
| 6 | 4.0 | 72.2 | 81.4 | 22.1 | 0.49 | 0.57 |
| 7 | 3.8 | 70.1 | 78.5 | 21.0 | 0.52 | 0.55 |
| 8 | 2.0 | 18.3 | 35.0 | 18.2 | 0.28 | 0.47 |
| 9 | 2.1 | 20.1 | 40.0 | 18.4 | 0.33 | 0.52 |
| 10 | 2.3 | 20.2 | 22.0 | 18.1 | 0.18 | 0.53 |
| 11 | 2.9 | 60.2 | 65.3 | 20.4 | 0.54 | 0.54 |

The invention claimed is:

1. A process to prepare a self-reinforced starch composite, comprising:
   (A) uniformly mixing a matrix phase comprising one or a combination of the substances selected from the group consisting of oxidized starch, cationic starch, and esterified starch, and a particulate reinforced phase comprising cross-linked starch nanocrystals; and wherein the mass ratio of the matrix phase to the particulate reinforced phase is between 4:0.01 and 4:1; and
   (B) adding the uniform mixture prepared in step (A) into a double screw extruder, heating and kneading the mixture; inputting pure water in an amount of 0.5%-25% of the mixture by weight, thus forming a processable thermoplastic material; and extruding the thermoplastic material into granules or sheets of self-reinforced material or further processing the thermoplastic material into a film.

2. The process of claim 1 wherein the matrix phase is one or a combination of the substances selected from the group consisting of oxidized starch, cationic starch, and esterified starch made from corn, potato, cassava, wheat, mung bean, and rice.

3. The process of claim 1 wherein said particulate reinforced phase is a cross-linked starch or starch nanocrystals wherein
   said cross-linked starch is one or a combination of the substances selected from the group consisting of potato, cassava, wheat, mung bean starch, and rice,
   said starch nanocrystal is one or a combination of nanocrystals selected from the group consisting of nanocrystals from corn starch, potato starch, cassava starch, wheat starch, mung bean starch, and rice starch, and
   the particle size of the starch nanocrystals is 10-200 nm.

4. The process of claim 1 wherein the pure water is deionized or purified water.

5. The process of claim 1 wherein the modified starch content accounts for 98.0%-99.5% of the mixture; cross-linked starch or starch nanocrystals accounts for 0.5%-2% of the mixture, and pure water accounts for 10-20% of the mixture.

6. The process of claim 1 wherein:
   (1) each part of the double screw extruder along the direction of the screw is heated to different temperature;
   (2) granules and sheets are prepared through direct extrusion at an extrusion pressure of 50-2000 N/m$^2$; and
   (3) the film is prepared by tape casting using a casting roller, and the rotation speed of the casting roller is set to 1-20 rpm.

7. The process of claim 1 wherein the heating is conducted at a temperature of less than 160° C.

8. A soft capsule made of the self-reinforced starch composite prepared using the process of claim 1.

* * * * *